United States Patent [19]
Moretz et al.

[11] Patent Number: 5,315,717
[45] Date of Patent: * May 31, 1994

[54] MULTI-LAYER MOISTURE MANAGEMENT FABRIC AND GARMENTS INCORPORATING A MOISTURE MANAGEMENT PANEL

[76] Inventors: Herbert L. Moretz, 20205 Lola Cir., Davidson, N.C. 28036; Daniel L. Brier, 1645 Lake Shore Dr., Denver, N.C. 28037

[*] Notice: The portion of the term of this patent subsequent to Jun. 8, 2010 has been disclaimed.

[21] Appl. No.: 994,114

[22] Filed: Dec. 21, 1992

Related U.S. Application Data

[62] Division of Ser. No. 791,066, Nov. 12, 1991, Pat. No. 5,217,782.

[51] Int. Cl.$^5$ ............................................. A41B 9/00
[52] U.S. Cl. ............................................. 2/400; 2/403; 2/406; 604/358; 604/378
[58] Field of Search .................. 2/400, 402, 403, 404, 2/405, 406; 604/358, 378; 428/913, 252, 253, 91, 97

[56] References Cited

U.S. PATENT DOCUMENTS

| | | | |
|---|---|---|---|
| 3,508,550 | 4/1970 | Vollrath | 2/400 |
| 3,714,946 | 2/1973 | Rudes | 2/400 |
| 3,720,212 | 3/1973 | Kaupin | 604/378 |
| 4,844,965 | 7/1989 | Foxman | 428/91 |
| 5,021,280 | 6/1991 | Farnworth et al. | 428/102 |
| 5,037,409 | 8/1991 | Chen et al. | 604/358 |
| 5,217,782 | 6/1993 | Moretz et al. | 604/358 |

OTHER PUBLICATIONS

Industrial Fabric Opportunities for Hydrophilic Nylon, Judy Peters, 1990.

*Primary Examiner*—Clifford D. Crowder
*Assistant Examiner*—Gloria Hale
*Attorney, Agent, or Firm*—W. Thad Adams, III

[57] ABSTRACT

A multi-layer moisture management fabric for being placed in garments. The multi-layer fabric includes a relatively thick inner moisture permeable hydrophobic fabric layer having for being positioned next to the skin of the wearer of the garment, a first, relatively thin intermediate hydrophilic fabric layer positioned adjacent the hydrophobic fabric layer on the side thereof away from the skin of the wearer, and a second, relatively thick outer hydrophilic fabric layer positioned adjacent the first hydrophilic fabric layer on the opposite side thereof from the hydrophobic fabric layer.

7 Claims, 10 Drawing Sheets

MULTI-LAYER MOISTURE MANAGEMENT FABRIC AND GARMENTS INCORPORATING A MOISTURE MANAGEMENT PANEL

This application is a division of application Ser. No. 07/791,066, filed on Nov. 12, 1991.

TECHNICAL FIELD AND BACKGROUND OF THE INVENTION

This invention relates to a multi-layer moisture management fabric and garments incorporating a moisture management panel. The invention as claimed and disclosed has particular application in undergarments for controlling leakage and spotting caused by minor to moderate urinary incontinence and in colostomy patients.

The invention also has application in many types of athletic apparel where perspiration-soaked garments next to the skin over a period of time can cause chafing, irritation and conditions conducive to bacteria, fungus and yeast growth. The multi-layer fabric and garments incorporating panels constructed of the multi-layer fabric are specifically intended to be essentially normal in outer appearance from similar garments without such panels. For this reason the invention uses combinations of fibers which are intended to remove moisture from the area of the skin and disperse the moisture into areas away from the skin in relatively thin layers, rather than concentrating the moisture away from the skin in a relatively small area, as is the case in many disposable urinary incontinence products.

At the same time, the fabric permits minor to moderate amounts of liquid to be dispersed without penetrating the garment's outer layer, thus preventing spotting or staining of the garment or of other garments worn over the garment.

Thus, the invention departs from the teachings of the prior art exemplified in the Vollrath U.S. Pat. No. 3,508,550. Vollrath discloses the placement of absorbent cotton panels inside a undergarment and next to the skin. The moisture is absorbed into and held in the cotton layer next to the skin. This is a serious functional weakness, since the moisture next to the skin creates a cold, clammy sensation as well as promoting bacterial growth.

SUMMARY OF THE INVENTION

Therefore, it is an object of the invention to provide a multi-layer fabric which has moisture management characteristics.

It is another object of the invention to provide a multi-layer fabric which can be fabricated into panels.

It is another object of the invention to provide a multi-layer fabric which can be incorporated into the crotch area of undergarments, pajamas, athletic apparel and the like.

It is another object of the invention to provide a multi-layer fabric which wicks moisture away from an adjacent body surface.

It is another object of the invention to provide a multi-layer fabric which has adjacent layers of hydrophobic and hydrophilic fabrics which exert a simultaneous push-pull effect on moisture to thereby move the moisture from one side of the adjacent layers to the other side.

It is another object of the invention to provide a multi-layer fabric which incorporates one o more layers which are moisture vapor permeable and liquid impermeable.

It is another object of the invention to provide garments such as undergarments, pajamas and athletic apparel which incorporate multi-layer fabrics having moisture control properties therein.

It is another object of the invention to provide garments such as undergarments, pajamas and athletic apparel which incorporate multi-layer fabrics having moisture control properties therein and which are essentially indistinguishable in outward appearance from conventional garments of a similar type.

These and other objects of the present invention are achieved in the preferred embodiments disclosed below by providing a multi-layer moisture management fabric for being placed in garments. The multi-layer fabric includes a relatively thick inner moisture permeable hydrophobic fabric layer having for being positioned next to the skin of the wearer of the garment, a first, relatively thin intermediate hydrophilic fabric layer positioned adjacent the hydrophobic fabric layer on the side thereof away from the skin of the wearer, and a second, relatively thick outer hydrophilic fabric layer positioned adjacent the first hydrophilic fabric layer on the opposite side thereof from the hydrophobic fabric layer.

According to one preferred embodiment of the invention, the hydrophobic fabric layer is formed of polyester fiber.

According to another preferred embodiment of the invention, hydrophobic fabric layer is formed of polyester fiber, and further wherein the fabric layer is brushed.

According to yet another preferred embodiment of the invention, the first, relatively thin hydrophilic fabric layer is formed of hydrophilic nylon fiber.

According to yet another preferred embodiment of the invention, the second, relatively thick hydrophilic fabric layer is formed of hydrophilic nylon fiber, and the fabric layer is brushed to raise a moisture trapping and conveying nap.

According to another preferred embodiment of the invention, a hydrophilic moisture vapor permeable and liquid impermeable membrane is positioned adjacent the second hydrophilic fabric layer on the side thereof opposite the first hydrophilic fabric layer.

According to yet another preferred embodiment of the invention, the fabric comprises a crotch panel positioned in the crotch area of a garment having a crotch.

According to one preferred embodiment of the invention, the garment comprises a man's brief.

According to another preferred embodiment of the invention, the garment comprises a man's boxer short or pajama bottom.

According to yet another preferred embodiment of the invention, the garment comprises a woman's panty.

Preferably, the inner hydrophobic fabric layer and the intermediate hydrophilic fabric layer are integrally formed by weaving a hydrophilic fabric with brushed hydrophobic fibers positioned on one surface thereof.

According to one preferred embodiment of the invention, the multi-layer fabric is incorporated into a fabric garment, and the vapor permeable membrane is bonded to the fabric of the garment.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Multi-Layer Fabric for Minor Incontinence and Athletic Uses

Figure 1:
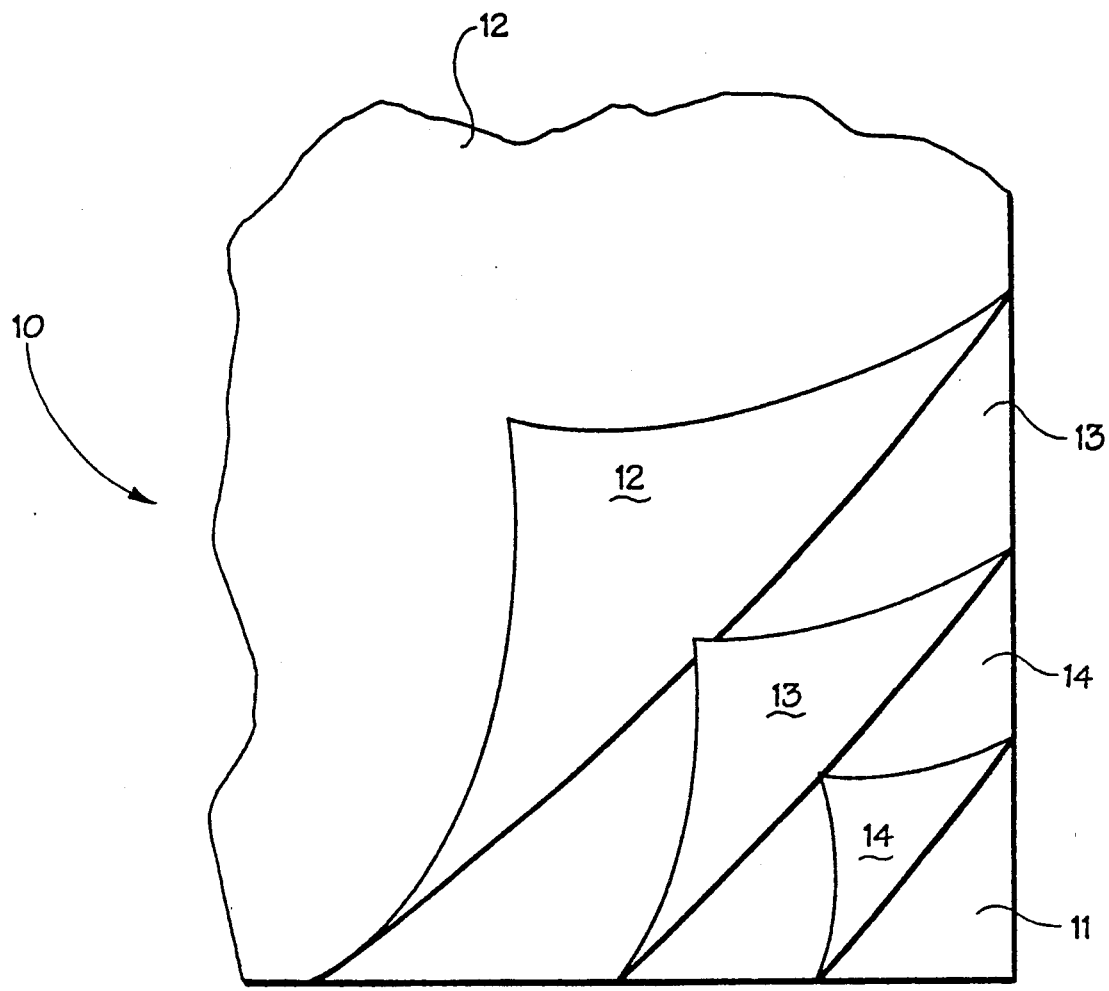
FIG. 1 is a plan of a section of a multi-layer fabric according to an embodiment of the invention, with the individual layers successively peeled away for clarity.

Referring now specifically to the drawings, a multi-layer fabric according to one embodiment of the present invention is illustrated in FIG. 1 and shown generally at reference numeral 10. The multi-layer fabric is shown laid over a shell fabric 11 which is ordinarily the fabric of the garment into which the multi-layer fabric 10 is incorporated. Thus, the multi-layer fabric 10 itself is formed of a relatively thick inner moisture permeable hydrophobic fabric layer 12, a first, relatively thin intermediate hydrophobic fabric layer 13 and a second, relatively thick outer hydrophilic fabric layer 14 which is positioned adjacent the first hydrophilic layer on the side opposite the hydrophobic layer 12.

Figures 3, 4:
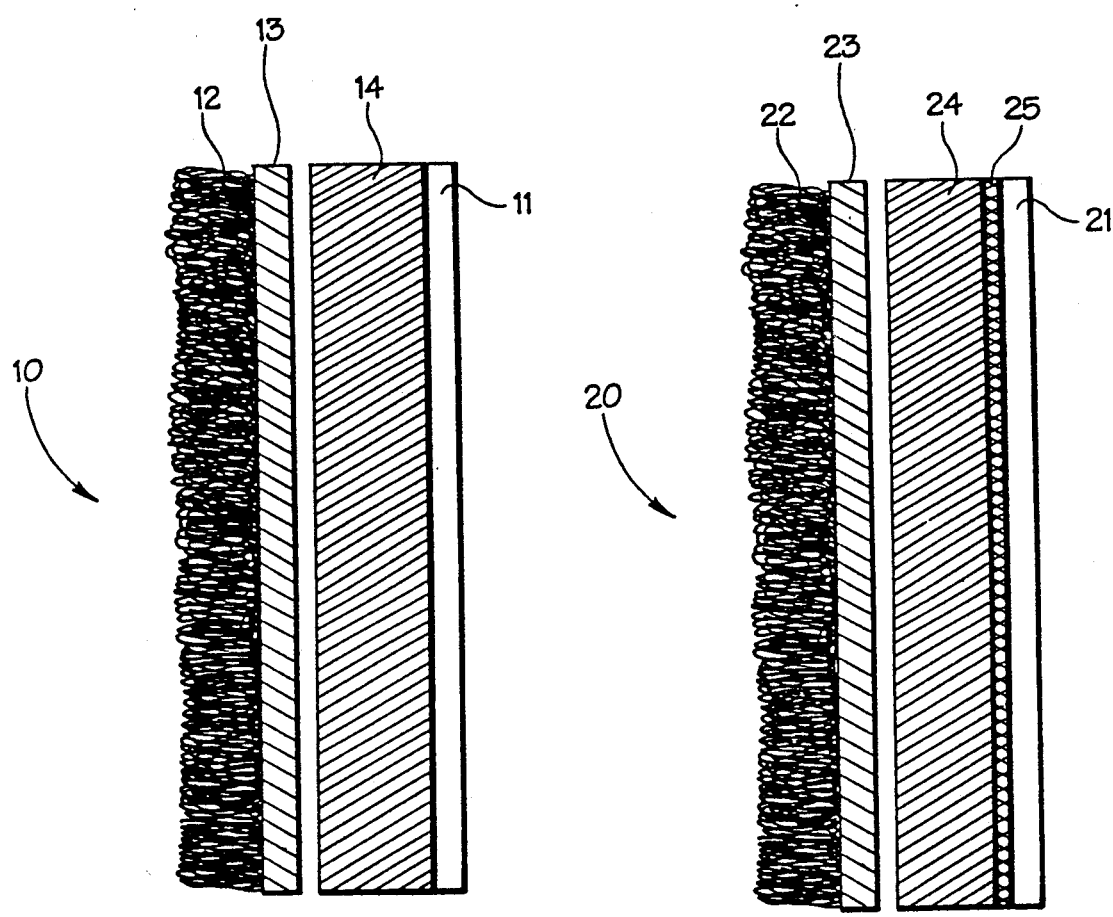
FIG. 3 is a cross-section of the panel shown in FIG. 1.
FIG. 4 is a cross-section of the panel shown in FIG. 2.

The hydrophobic layer 12 is intended to be next to and in contact with the skin of the garment wearer, with the outer hydrophilic layer 14 next to the shell fabric 11 from which the garment itself is constructed, as is illustrated in FIG. 3.

The hydrophobic layer 12 is constructed of a suitable non-absorbent fiber such as polyester. The adjacent hydrophilic layer 13 is formed of a highly absorbent fiber such as Hydrofil brand nylon fiber marketed by Allied Fibers. This fiber is characterized by a very low denier and results in a very supple, flexible and drapeable fabric. It has the strength, durability, ease of care and styling characteristics of nylon combined with absorbency somewhat better than cotton. The absorbency of this nylon is defined by its structure which permits moisture to be held on the greater surface area of the fibers and in the fabric interstices of fabrics woven with the low denier fibers. In contrast, cotton achieves its absorbency by taking the moisture into the fiber itself. Hydrofil nylon is a block copolymer of nylon 6 (approx. 85%) and polyethylene oxide diamine (approx. 15%) and for this reason is referred to as a nylon even though it contains significant amounts of other material.

As an alternative construction the layers 12 and 13 may be formed as a single fabric with the hydrophilic polyester 12 being a surface layer of a underlying base fabric layer 13 woven of the hydrophilic nylon. Preferably the hydrophobic layer 12 is brushed or buffed to raise a nap which aids in wicking the moisture away from the skin and into the hydrophilic layer 13.

The hydrophilic layer 14 is also preferably constructed of a highly absorbent fiber such as Hydrofil brand nylon fiber marketed by Allied Fibers. Layer 14 is woven with a brushed or buffed inner surface next to the outer surface of hydrophilic layer 13. Hydrophilic layer 13 is intended primarily as a "transport" layer which pulls the moisture from the hydrophobic layer 12 and the underlying skin. Hydrophilic layer 14 is intended primarily as a "storage" layer and for this reason is brushed or buffed to present more surface area to the moisture. The moisture is absorbed into the highly absorbent fibers and held there away from the skin and away from the outer garment shell layer 11.

The multi-layer fabric 10 described above and illustrated in FIGS. 1 and 3 is intended primarily for minor incontinence and for use in athletic apparel where the moisture release is minimal and relatively gradual.

Increased moisture control can be obtained by increasing the thickness or density of the inner hydrophobic layer 12 and/or the hydrophilic layer 13 by a factor of, for example, 1.3. The thickness or density of the outer hydrophilic layer 14 is preferably increased by a factor of 1.5. Either thickness or density or a combination of both can be utilized since the object is to provide greater fiber surface areas for moisture absorption. Various highly absorbent materials, either natural or synthetic, or combination thereof, may be used.

In addition, the outer hydrophilic layer 14 can be treated with a moisture resistant, breathable material such as tetrafluoroethylene in order to permit evaporation yet prevent liquid penetration into the shell layer 11 of the garment. The structure of this embodiment is also illustrated in FIGS. 1 and 3.

Multi-Layer Fabric for Moderate Incontinence

Figure 2:
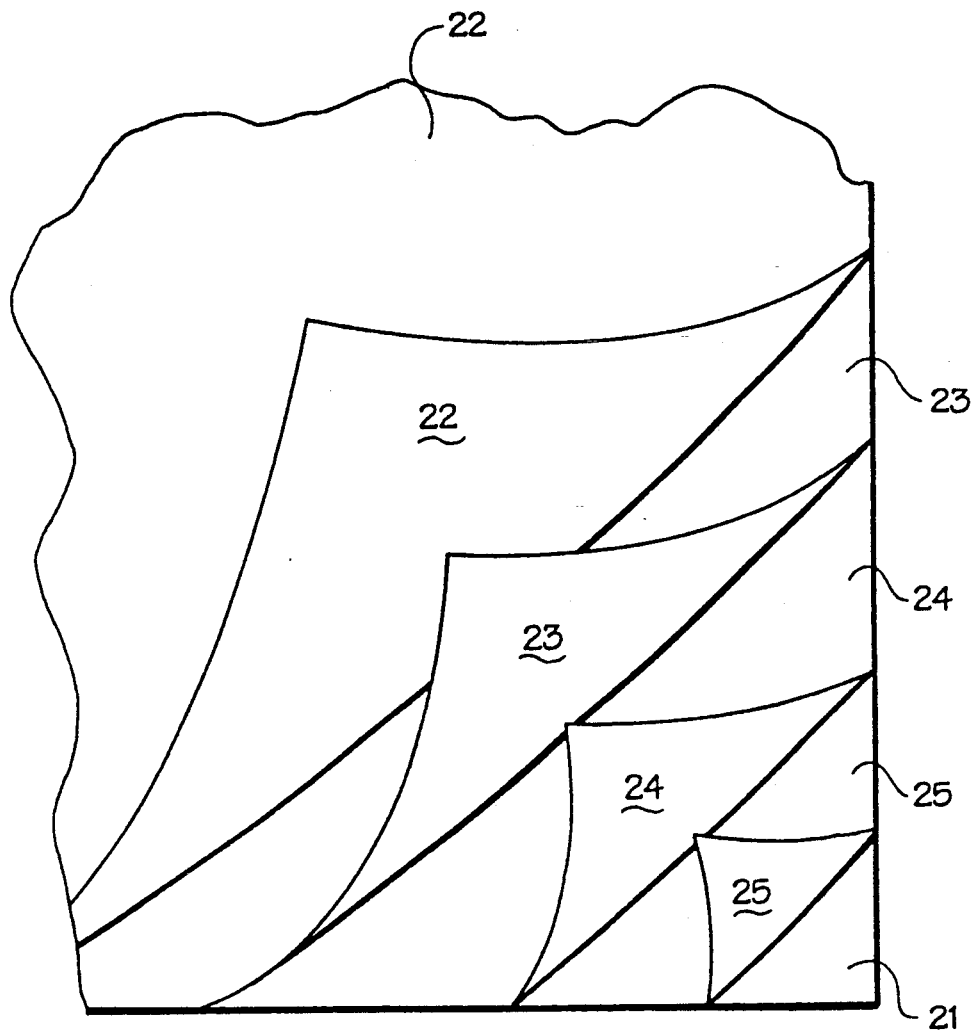
FIG. 2 is a plan of a section of a multi-layer fabric according to another embodiment of the invention, with the individual layers successively peeled away for clarity.

An embodiment of the multi-layer fabric designed especially for moderate incontinence is illustrated in FIGS. 2 and 4 and indicated at broad reference numeral 20. As is shown in FIG. 2, the material of the garment itself is indicated at 21.

The multi-layer fabric 20 is formed of a relatively thick inner moisture permeable hydrophobic fabric layer 22, a first, relatively thin intermediate fabric layer 23 and a second, relatively thick outer hydrophilic fabric layer 24 which is positioned adjacent the first hydrophilic layer 23 on the side opposite the hydrophobic layer 22.

The hydrophobic layer 22 is intended to be next to and in contact with the skin of the garment wearer, with the outer hydrophilic layer 24 being positioned away from the skin.

A membrane layer 25, such as Gore-Tex brand or Sympatex brand moisture resistant membranes manufactured by W. L. Gore & Associates and Akzo Fibers, Inc., respectively, is bonded to the shell fabric 21 from which the garment itself is constructed, as is illustrated in FIG. 4.

The hydrophobic layer 22 is constructed of a suitable non-absorbent fiber such as polyester. For purposes of comparison the layer 22 can be approximately 1.5 times the thickness and/or density of the comparable layer 12 of the multi-layer fabric 10 described above. The adjacent hydrophilic layer 23 is formed of a highly absorbent fiber such as Hydrofil brand nylon fiber marketed by Allied Fibers. For purposes of comparison the layer 23 may be 1.7 times the thickness and/or density of the comparable layer 13 of the multi-layer fabric 10 described above.

As an alternative construction the layers 22 and 23 may be formed as a single fabric with the hydrophilic polyester 22 being a surface layer of an underlying base fabric layer 23 woven of the hydrophilic nylon. Preferably, the hydrophobic layer 22 is brushed or buffed to raise a nap which aids in wicking the moisture away from the skin and into the hydrophilic layer 23.

The hydrophilic layer 24 is also preferably constructed of a highly absorbent fiber such as Hydrofil brand nylon fiber marketed by Allied Fibers. Layer 24 is wove with a brushed or buffed inner surface next to the outer surface of hydrophilic layer 23.

Hydrophilic layer 23 is intended primarily as a "transport" layer which pulls the moisture from the hydrophobic layer 22 and the underlying skin. Hydrophilic layer 24 is intended primarily as a "storage" layer and for this reason is brushed or buffed to present more surface area to the moisture. The moisture is absorbed into the highly absorbent fibers and held there away from the skin and away from the outer garment shell layer 21.

The membrane layer 25 prevents liquid moisture from penetrating to the surface of the garment while permitting vapor transfer through the membrane 25 and outer shell fabric 21, in order to facilitate evaporation.

Garments Incorporating Multi-Layer Moisture Management Panels

Figure 5:
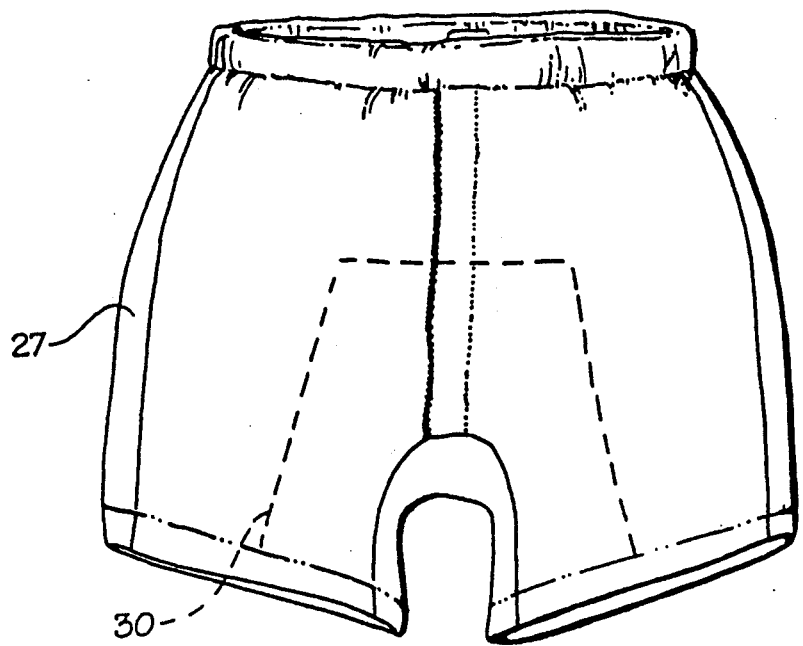
FIGS. 5 and 6 are front and rear views of a man's boxer short with a panel of the multi-layer fabric shown in FIGS. 1 and 3.
Figure 6:
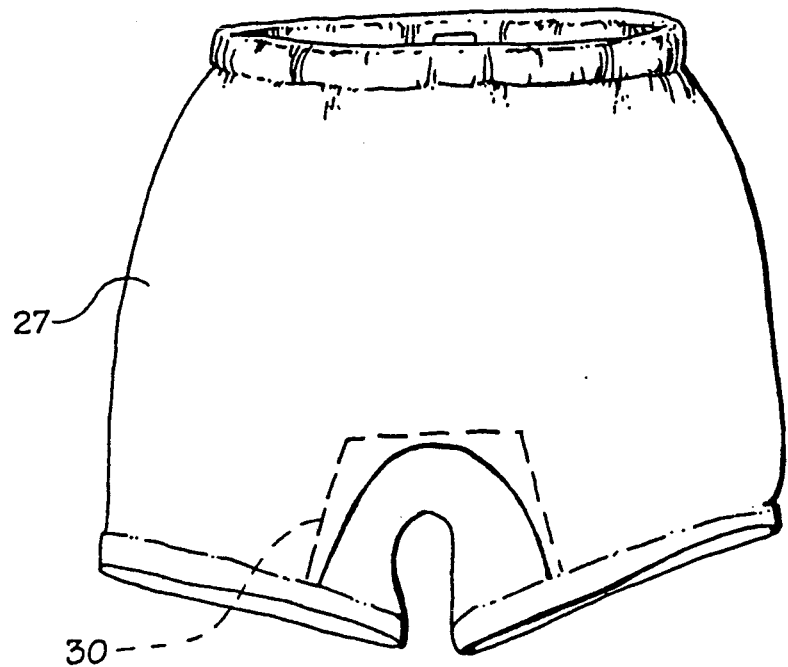
Figure 7:
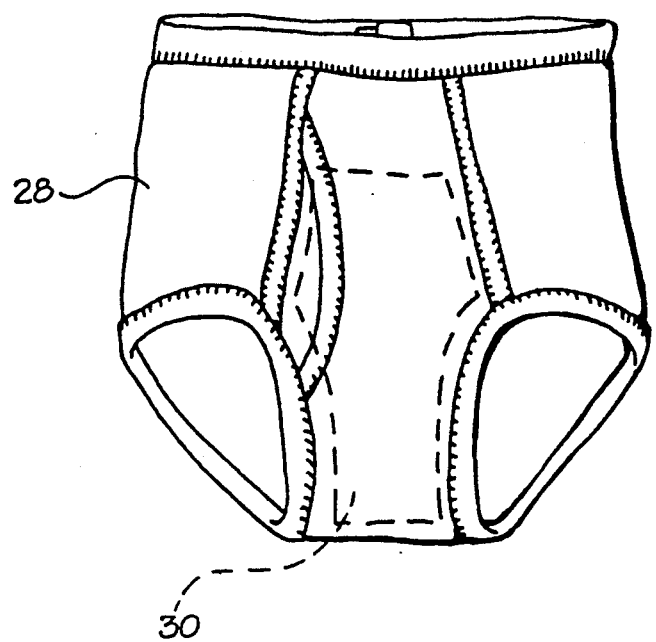
FIGS. 7 and 8 are front and rear views of a man's brief with a panel of the multi-layer fabric shown in FIGS. 1 and 3.
Figure 8:
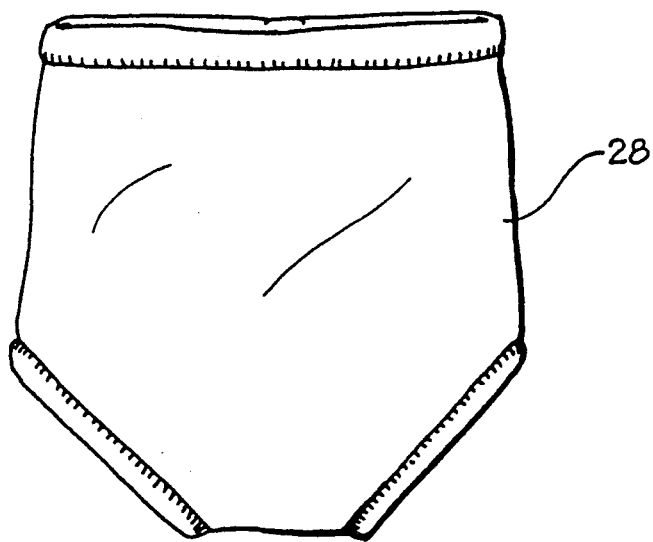
Figure 9:
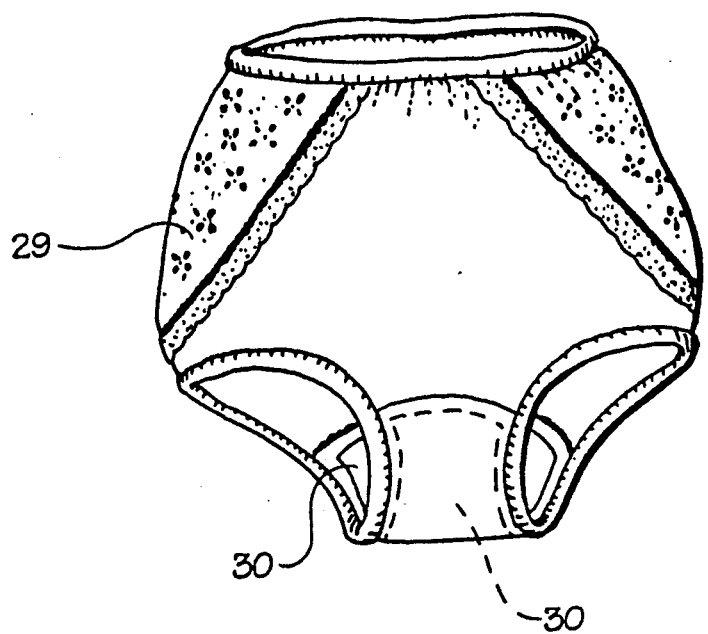
FIGS. 9 and 10 are front and rear views of a woman's panty with a panel of the multi-layer fabric shown in FIGS. 1 and 3.
Figure 10:
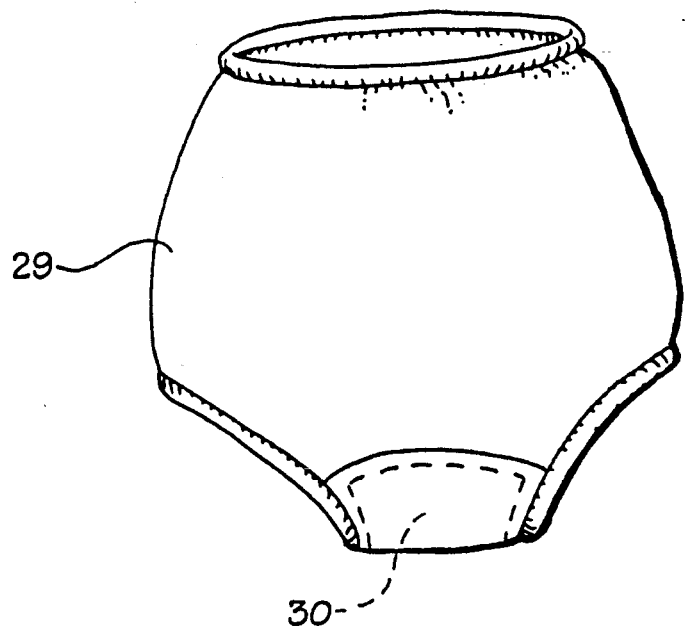
Figure 11:
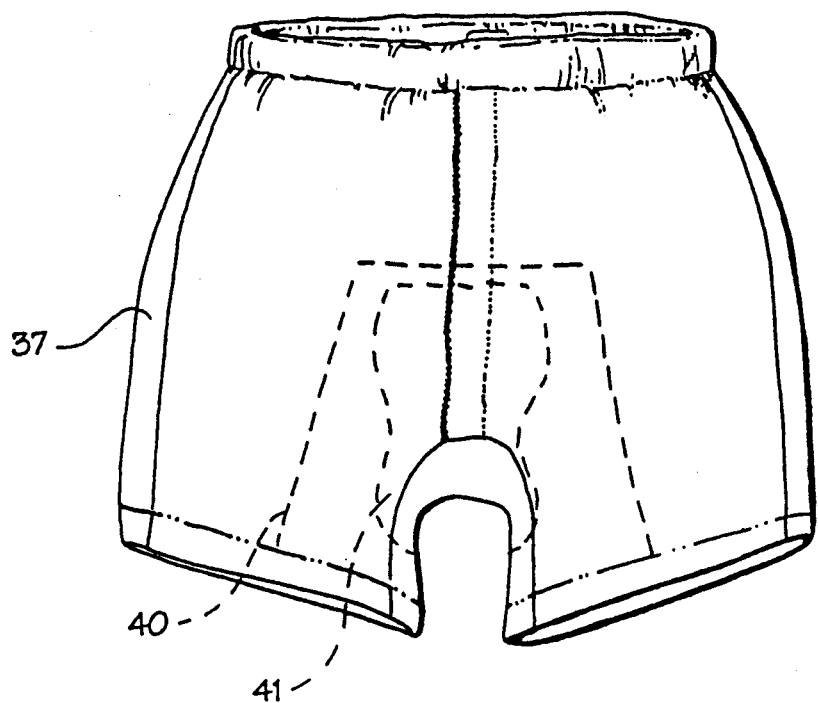
FIGS. 11 and 12 are front and rear views of a man's boxer short with a panel of the multi-layer fabric shown in FIGS. 2 and 4.
Figure 12:
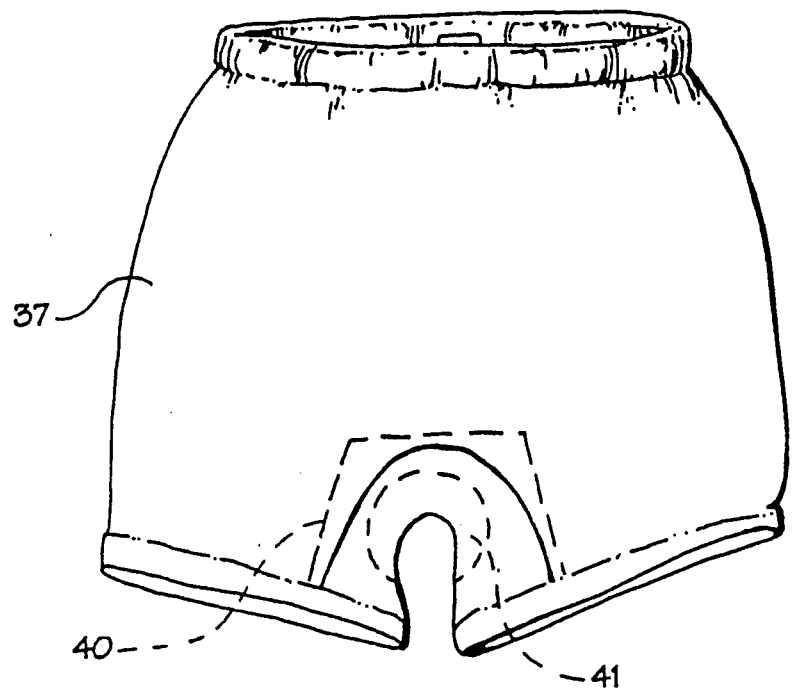
Figure 13:
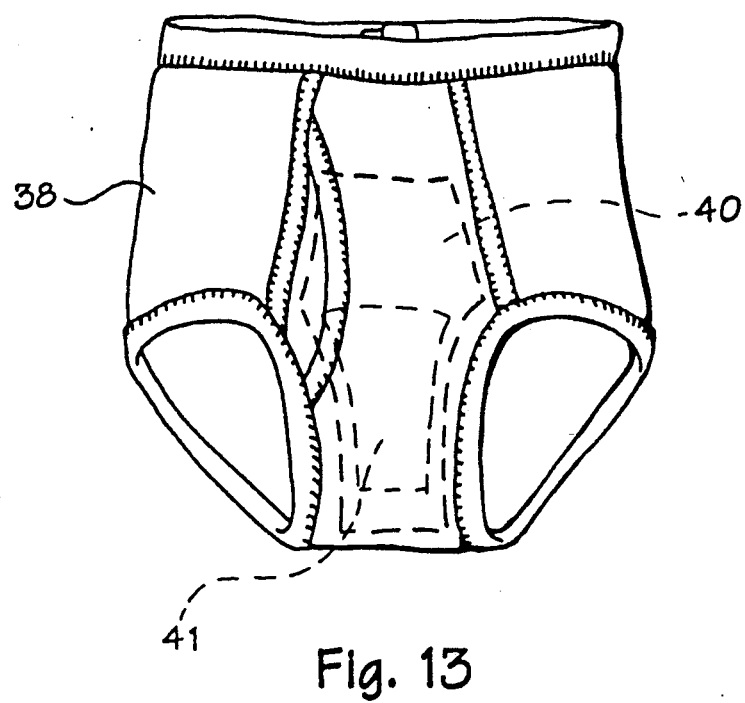
FIGS. 13 and 14 are front and rear views of a man's brief with a panel of the multi-layer fabric shown in FIGS. 2 and 4.
Figure 14:
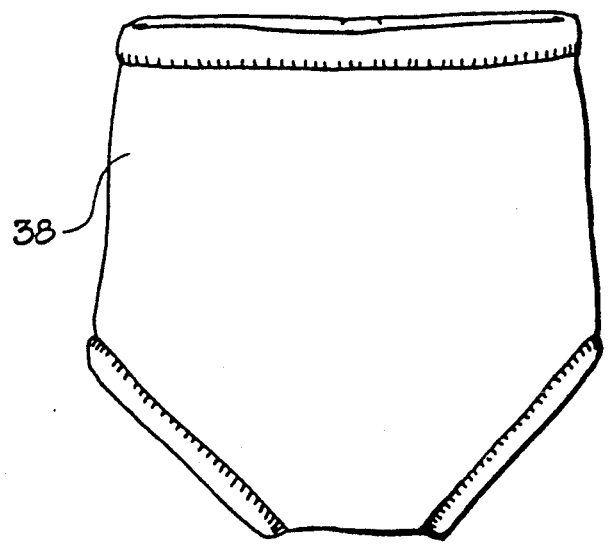
Figure 15:
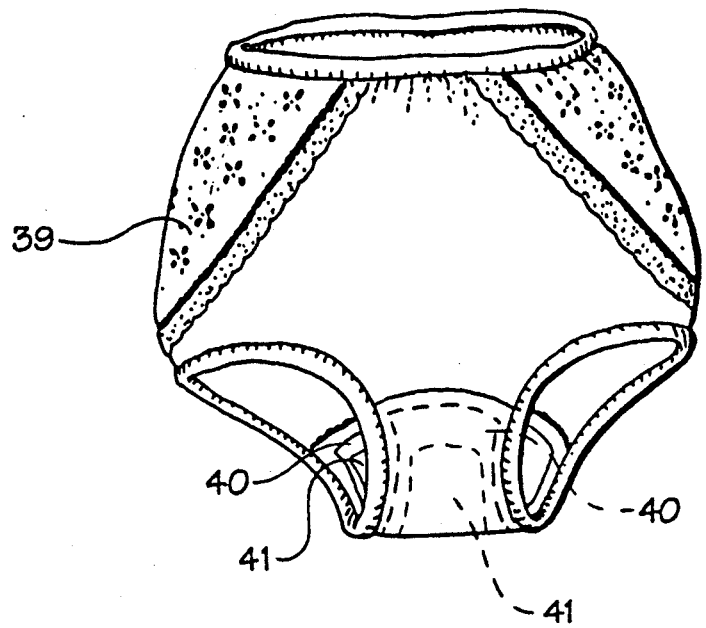
FIGS. 15 and 16 are front and rear views of a woman's panty with a panel of the multi-layer fabric shown in FIGS. 2 and 4.
Figure 16:
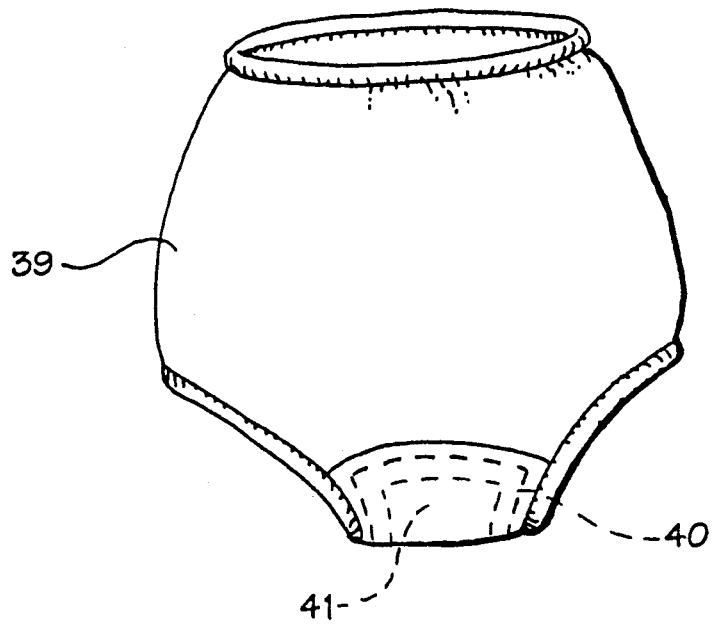
Figure 17:
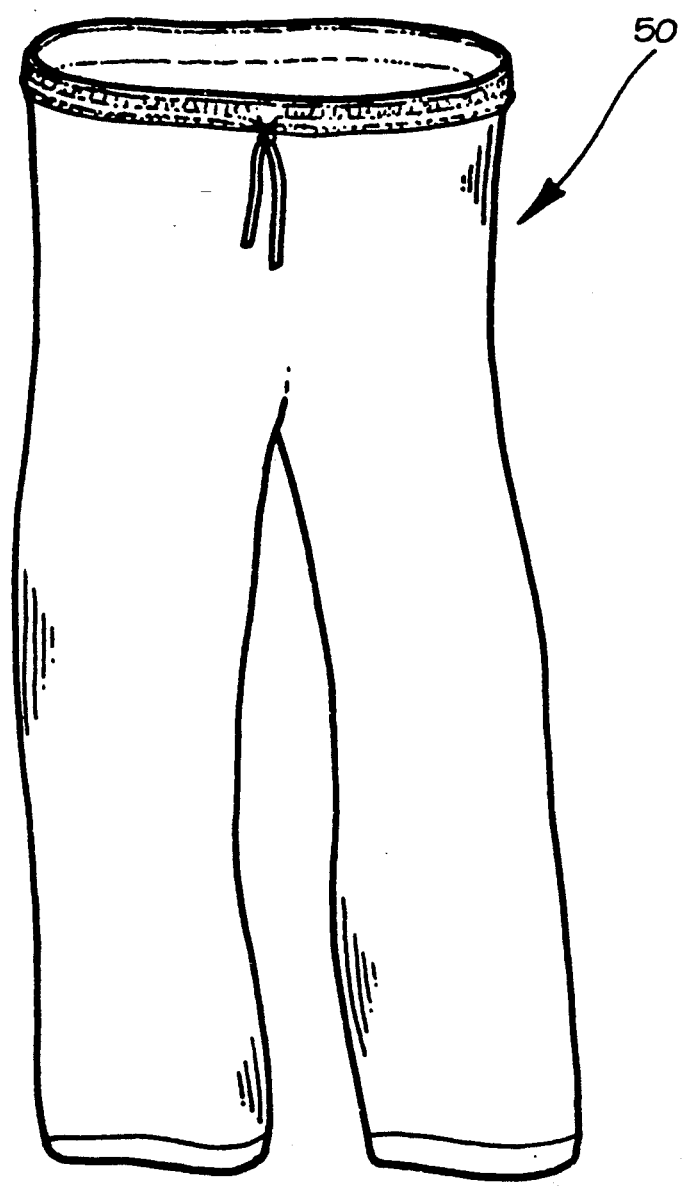
FIG. 17 is a perspective view of a pajama bottom.

Referring now to FIGS. 5-10, garments incorporating the multi-layer fabric 10 and intended for minor incontinence and athletic uses are illustrated. FIGS. 5, 7 and 9 illustrate the front of men's boxer shorts 27, briefs 28 and women's panties 29, respectively. In each case a panel 30 formed of the multi-layer fabric 10 is sewn into the inside of the garment. The entire panel 30 is relatively thin—on the order of 3 mm or less and is essentially invisible from the outside. Construction of the panel 30 results in a multi-layer fabric which has the same handling characteristics as the garment itself. FIGS. 6, 8 and 10 illustrate the back of the garments 27, 28 and 29.

FIGS. 11-17 illustrate garments incorporating the multi-layer fabric 20 and intended for moderate incontinence. FIGS. 11, 13, 15 and 17 illustrate the front of men's boxer shorts 37, briefs 38, women's panties 39 and pajama bottoms 50, respectively. In each case a panel 40 formed of the multi-layer fabric 10 is sewn into the inside of the garment. Optionally, one or more additional layers 41 of the hydrophilic layer 24 may be incorporated into the garments. Preferably, the layer or layers 41 are smaller and are positioned in the area most likely to receive the maximum amount of liquid. Reducing the size of the layer 41 also somewhat reduces the weight and bulk of the garment. Although not shown, provision can be made for the placement of separate, disposal absorbent pads into the women's panties 29 and 39.

In summary, the multi-layer fabrics 10 and 20, and garments 27-29 and 37-39, inclusive provide efficient wicking of moisture away from the skin, thereby maintaining the most comfortable and dry environment possible next to the skin. This naturally promotes a healthful condition next to the skin. The multi-layer fabrics 10 and 20 quickly spread the wetness through the absorptive layer in order to prevent it concentration in a relatively small area which could soak through and spot or stain outer garments. In addition, the multi-layer fabric 20 provides additional wicking and absorptive capacity, as well as a protective moisture repellent but otherwise breathable shield against excess wetness which might otherwise soak into outer garments.

While the multi-layer fabrics described above have been referred to as being woven, alternative constructions which are knitted or formed of non-woven bonded layers is also possible. In addition, attachment methods other than sewing can be used to secure the panels into the garments.

Moisture management multi-layer fabrics and garments incorporating multi-layer fabrics are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A reusable, launderable garment, said garment including a multi-layer moisture management fabric incorporated therein, said moisture management fabric comprising:

(a) a relatively thick knitted or woven inner moisture permeable hydrophobic fabric layer for being positioned next to the skin of the wearer of the garment;

(b) a first, relatively thin knitted or woven intermediate hydrophilic fabric layer positioned adjacent the hydrophobic fabric layer on the side thereof away from the skin of the wearer; and (c) a second, relatively thick knitted or woven outer hydrophilic moisture permeable fabric layer positioned adjacent the first hydrophilic fabric layer on the opposite side thereof from the hydrophobic fabric layer.

2. In a multi-layer garment according to claim 1, wherein said garment comprises a crotch panel positioned in the crotch area of a garment having a crotch.

3. A multi-layer garment according to claim 1, wherein said garment comprises a man's brief.

4. A multi-layer garment according to claim 1, wherein said garment comprises a man's boxer short or pajama bottom.

5. A multi-layer garment according to claim 1, wherein said garment comprises a woman's panty.

6. A multi-layer garment according to claim 1, wherein said inner hydrophobic fabric layer and said intermediate hydrophilic fabric layer are integrally formed by weaving a hydrophilic fabric with brushed hydrophobic fibers positioned on one surface thereof.

7. A multi-layer garment according to claim 1 in combination with a fabric garment, wherein said second fabric layer comprises a vapor permeable membrane bonded to the fabric of the garment.

* * * * *